United States Patent [19]

Atkinson et al.

[11] 3,968,236

[45] July 6, 1976

[54] 2-AMINOMETHYL-5-HYDROXY-4H-PYRAN-4-ONE AND DERIVATIVES THEREOF

[75] Inventors: Joseph G. Atkinson, Montreal; Joshua Rokach, Laval; Clarence S. Rooney, Beaconsfield, all of Canada

[73] Assignee: Merck & Co., Inc., Rahway, N.J.

[22] Filed: Jan. 22, 1975

[21] Appl. No.: 542,977

[52] U.S. Cl............................. 424/283; 260/345.7; 260/345.9
[51] Int. Cl.² ................. C07D 309/22; A01N 9/28
[58] Field of Search...................... 260/345.7, 345.9; 424/283

[56] References Cited
UNITED STATES PATENTS

| | | | |
|---|---|---|---|
| 2,865,930 | 12/1958 | Metiuier et al. | 260/345.9 |
| 2,918,402 | 12/1959 | Fredrick | 260/345.9 |
| 3,008,971 | 11/1961 | Parker et al. | 260/345.9 |
| 3,029,256 | 4/1962 | Cook | 260/345.9 |

*Primary Examiner*—James O. Thomas, Jr.
*Assistant Examiner*—G. Breintenstein
*Attorney, Agent, or Firm*—James A. Arno; William H. Nicholson; Harry E. Westlake, Jr.

[57] ABSTRACT

The 2-aminomethyl-5-hydroxy-4H-pyran-4-ones of the present invention are disclosed to have pharmaceutical utility as skeletal muscle relaxants. Also disclosed are processes for the preparation of such pyranones; pharmaceutical compositions comprising such compounds; and method of treatment comprising administering such compounds and compositions when a muscle relaxant effect is indicated.

6 Claims, No Drawings

2-AMINOMETHYL-5-HYDROXY-4H-PYRAN-4-ONE AND DERIVATIVES THEREOF

BACKGROUND OF THE INVENTION

This invention relates to 2-aminomethyl-5-hydroxy-4H-pyran-4-one and certain derivatives thereof, especially the amide derivatives, which are useful as skeletal muscle relaxants. The invention also relates to processes for the preparation of such compounds; to pharmaceutical compositions comprising such compounds; and to methods and treatment comprising administering such compounds and compositions when a muscle relaxant effect is indicated.

The 2-aminomethyl-5-hydroxy-4H-pyran-4-ones of the present invention may be represented generically by the following structural formula (I):

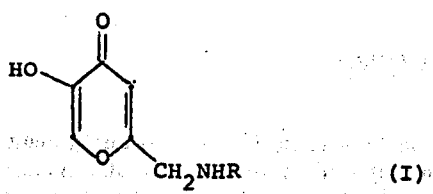

wherein R is hydrogen, or R represents an acyl moiety derived from a carboxylic acid especially an α-amino acid.

Unexpectedly, it has been discovered that the above-described pyranones of the present invention are useful as skeletal muscle relaxants and can be used for treating muscle spasms and other similar muscle disorders associated with or caused by injury or arising spontaneously with no known cause. Muscle spasm, spasticity and related clinical disorders involving muscle hyperactivity or increased muscle tone affect a large section of the population. Such clinical disorders involving muscle hyperactivity include the spasticity of cerebral origin which may arise from brain injury or tumor. Another related disorder is cerebral palsy. Other clinical disorders involving tonic skeletal muscle hyperactivity are Parkinson's disease, muscular rigidity and muscle spasm of traumatic origin including low-back and cervical spine syndromes, many orthopedic deformities, arthritic states, myositis, whip-lash injuries, fractures, dislocation, cramps, sciatica, and spinal cord injuries. At present a variety of medicinals are used in an attempt to relieve or correct the clinical disorders involving muscle hyperactivity including muscle spasm and spasticity and pain associated therewith. But administration of these various materials unfortunately is attended by concomitant side effects and toxicity and/or lack of specificity which limit their usefulness. There is an unsatisfied need at the present time for a medication which has a high specific effect on the muscle hyperactivity associated with various clinical disorders when administered either by the oral or parenteral route which at the same time has a minimum of side effects or contraindications.

Accordingly it is an object of the present invention to provide the above-described pyranones which are useful as skeletal muscle relaxants. It is a further object of the present invention to provide pharmaceutical compositions comprising such pyranones and to provide methods of treatment comprising administering such compounds and compositions when a skeletal muscle relaxant effect is indicated.

DETAILED DESCRIPTION OF THE INVENTION

In general, 2-aminomethyl-5-hydroxy-4H-pyran-4-ones of the present invention may conveniently be prepared from kojic acid [5-hydroxy-2-hydroxymethyl-4H-pyran-4-one], which is readily available. Blocking of the 5-hydroxy group as an ether derivative is necessary in some reactions and this can be carried out readily by reacting kojic acid with and alkyl or aralkyl halide such as benzyl halide (bromide or chloride) or the like in the presence of a strong base such as sodium methoxide and the like to form an alkyl ether which functions as a readily removable blocking group. This first step, protection of the 5-hydroxy group, is preferred in the preparation of the instant amide derivatives but is not necessary for the preparation of N-unsubstituted 2-aminomethyl-5-hydroxy-4H-pyran-4-one. There is no criticality as to the reaction temperature or solvent in this first step; for example, the conditions of A. F. Thomas and A. Marxer, *43 Helv. Chim. Acta* 469 (1960) have been found to be suitable for the preparation of such ether derivatives. In the second step, the 5-protected intermediate (or kojic acid) is converted to its tosylate (or other alkyl or aryl sulfonate) by reaction with tosyl chloride in the presence of a base such as pyridine. Such sulfonation reactions are well-known and there is no criticality to the instant procedure; for example, the procedure of A. F. Thomas, *J. Chem. Soc.* 439 (1962) has been found suitable. Conversion of the sulfonate ester thus formed to the amino group may be accomplished directly by reaction with ammonia, or indirectly, for example via the production of an azide by reaction of the sulfonate with sodium azide in a solvent such as dimethylformamide. The azide species thus formed is easily reduced to the amine by treatment with a reducing agent such as, for example, hydrobromic acid in acetic acid in the presence of a bromine trapping reagent such as acetone or phenol, or alternatively catalytic hydrogenolysis. The 5-blocking group is easily removed by acid hydrolysis and, in the hydrobromic acid/acetic acid procedure, is removed simultaneously with the reduction of the azide. In a more direct route to 2-aminomethyl-5-hydroxy-4H-pyran-4-one, 5-hydroxy-4H-pyran-4-on-2-ylmethyl chloride or its sulfonate ester can be converted to the azide which is then reduced to the desired amine, without involvement of the 5-protected intermediate. The following schematic diagram illustrates the above generally described process.

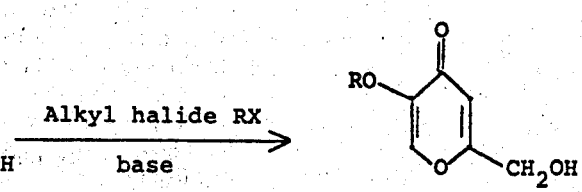

-continued tosylchloride (TsCl)
─────────────────→
pyridine

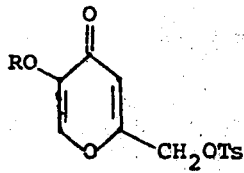

NaN₃
─────────────────→
DMF

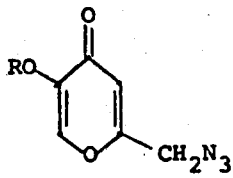

HBr/acetic acid
─────────────────→
trapping agent (phenol)

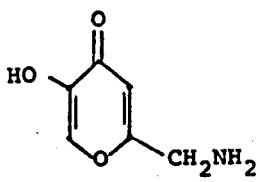

In addition to the free amine, 2-aminomethyl-5-hydroxy-4H-pyran-4-one (I), preferred embodiments of the present invention comprise amide derivatives of I. The most preferred amide derivatives are those formed from α-amino acids such as glycine and alanine, that is 2-amino-N-[(5-hydroxy-4H-pyran-4-on-2-yl)methyl] acetamide and 2-amino-N-[(5-hydroxy-4H-pyran-4-on-2-yl)methyl] propionamide, respectively. Such amides are formed by reaction of 2-aminomethyl-5-aralkyloxy-4H-pyran-4-one with suitable amine blocked amino acid intermediates by procedures well-known in peptide chemistry followed by removal of blocking groups. Thus for example, treating 2-aminomethyl-5-benzyloxy-4H-pyran-4-one with N-benzyloxycarbonylglycine p-nitrophenyl ester in isopropanol at reflux provides 2-benzyloxycarbonylamino-N-[(5-benzyloxy-4H-pyran-4-one-2-yl)methyl]acetamide which is readily hydrolyzed with hydrobromic acid in acetic acid to 2-amino-N-[(5-hydroxy-4H-pyran-4-on-2-yl)methyl]acetamide.

Also contemplated within the scope of the present invention are pharmaceutically acceptable salt, ester and amide derivatives of the pyranones of the present invention represented by structural formula I. Such pharmaceutically acceptable forms may be prepared by conventional means. Salt forms are the most preferred and include (relative to the amino nitrogen): the hydrochloride, hydrobromide, sulfate, phosphate, citrate, tartrate, succinate and the like; with respect to salts based upon acidic hydroxyl function, salts derived from the alkali and alkaline earth metals such as sodium and potassium are preferred. These pharmaceutically acceptable salt, ester and amide derivatives of I are generally equivalent in potency to the free amino form of I or the preferred amides thereof taking into consideration the stoichiometric quantities employed.

In the method of treatment and pharmaceutical composition aspects of the present invention it is to be noted that the precise unit dosage form and dosage level depend upon the case history of the individual being treated and consequently are left to the discretion of the therapist. In general, however, the compounds of the present invention produce the desired effect of skeletal muscle relaxation when given at from about 0.1 to about 30 mg/kg. body weight per day. Any of the usual pharmaceutical forms may be employed such as tablets, elexirs and aqueous suspensions comprising from about 0.1 to about 30.0 mg. of the compounds of this invention per kilogram body weight given daily. Thus for example tablets given 2–4 times per day comprising from about 0.5 to about 75.0 mg. of the compounds of this invention are suitable; however, the preferred range for the unit dosage level in the form of tablets is from about 2.0 to about 40.0 mg. of the compounds of the present invention. Sterile solutions for injection comprising from about 1 to about 30.0 mg. per dose of the compounds of this invention given 2–4 times daily are also a suitable means of delivery.

The following examples representatively illustrate but do not limit the product, compositional or method of treatment aspects of the present invention.

EXAMPLE 1

Preparation of
2-aminomethyl-5-hydroxy-4H-pyran-4-one

A mixture of 143 g. of 2-azidomethyl-5-hydroxy-4H-pyran-4-one, prepared according to the procedure reported in 9 J. Chem. and Eng. Data 228 (1964), and 72 g. phenol is dissolved in 700 ml. of acetic acid. The solution is cooled in an ice bath and saturated with HBr gas. After half an hour a precipitate appears which is stirred for three hours. The mixture is cooled with ice and filtered. The solid is washed first with acetic acid, then freely with tetrahydrofuran, and finally with ether. After drying, there is obtained 287 g. of the dihydrobromide of 2-aminomethyl-5-hydroxy-4H-pyran-4-one, m.p. 206°–207°C.

The resulting dihydrobromide (287 g.) is dissolved in 1.5 liters of methanol and 1 liter of tetrahydrofuran is added. The solution is concentrated to a low volume (500 cc.) by evaporation in vacuum and 1 liter of tetrahydrofuran added. The solid is filtered, yielding 154 g. of the monohydrobromide of 2-aminomethyl-5-hydroxy-4H-pyran-4-one, m.p. 220°–222°C.

Analysis calcd.: C, 32.43; H, 3.60; N, 6.36; Br, 36.03.
Analysis found: C, 32.40; H, 3.76; N, 6.58; Br, 36.01.

EXAMPLE 2

Preparation of
2-amino-N-[(5-hydroxy-4H-pyran-4-on-2-yl)-methyl] acetamide

A mixture of 5 grams of 2-aminomethyl-5-benzyloxy-4H-pyran-4-one and 7.5 grams of the commercially available N-benzyloxycarbonylglycine p-nitrophenyl ester in 120 ml. isopropanol is refluxed for 20 minutes. At the beginning the solution becomes clear and then the end product crystallizes out. The solid is filtered while hot, yielding 7 grams, m.p. 179°–180°, of the intermediate 2-benzyloxycarbonylamino-N-[(5-benzyloxy-4H-pyran-4-on-2-yl)methyl]acetamide.

The resulting intermediate (5 g.) is dissolved in 70 ml. acetic acid and the resulting solution is saturated with HBr and refluxed for 30 minutes. The material dissolves at first and the desired product (4 g.) precipitates in the form of the dihydrobromide. The dihydrobromide is recrystallized from methanol yielding 2.08 grams of the monohydrobromide of 2-amino-N-[(5-hydroxy-4H-pyran-4-on-2-yl)-methyl]acetamide, m.p. 216°–218°C.

Analysis calcd.: C, 34.40; H, 3.99; N, 10.00; Br, 28.65.

Analysis found: C, 34.68; H, 4.02; N, 10.40; Br, 29.08.

EXAMPLE 3

Preparation of 2-amino-N-[(5-hydroxy-4H-pyran-4-on-2-yl)-methyl]-propionamide

To a mixture of 5.04 g N-benzyloxycarbonyl-α-alanine, prepared by known methods [Ber. 65B, 1192–1201 (1932)], 60 ml methylene chloride and 4.5 ml triethylamine cooled at −5°C, is added 2.8 ml ethylchloroformate. The mixture is stirred for 5 minutes. To the resulting solution is added a mixture of 6.56 g 2-aminomethyl-5-benzyloxy-4H-pyran-4-one, 12 ml triethylamine and 60 ml methylene chloride. The mixture is stirred for 15 minutes at −5°C and 3 hours at 25°C, then extracted with dilute HCl, bicarbonate solution and then water. The organic layer is dried over $Na_2SO_4$ and evaporated to dryness. The residue is treated with ether and filtered to yield 7.75 g of the intermediate, 2-benzyloxycarbonylamino-N-[(5-benzyloxy-4H-pyran-4-on-2-yl)methyl]propionamide.

The resulting intermediate (7.7 g) is dissolved in 120 ml acetic acid; the solution is saturated with HBr and heated at 90°C for 25 minutes, evaporated to dryness, and then 50 ml acetic acid is added and again evaporated to dryness. The residue is triturated with ether and decanted. The residue is dissolved in the minimum amount of water at 25°C, extracted with ether, and the aqueous phase evaporated to dryness yielding 7.4 g of a semisolid which is passed through a DOWEX 50W-X8 resin (supplied by BIO-RAD Laboratories) by elution with 1N $NH_4OH$. The eluate is evaporated to dryness, dried at 85°C in high vacuum for 8 hours to yield 2.97 g of pure 2-amino-N-[(5-hydroxy-4H-pyran-4-on-2-yl)methyl]propionamide, m.p. 175°–178°C (dec.).

EXAMPLE 4

Pharmaceutical compositions

A typical tablet containing 5 mg. 2-aminomethyl-5-hydroxy-4H-pyran-4-one per tablet is prepared by mixing together with the active ingredient calcium phosphate, lactose and starch in the amounts shown in the tables below. After these ingredients are thoroughly mixed, the appropriate amount of magnesium stearate is added and the dry mixture blended for an additional three minutes. This mixture is then compressed into tablets weighing approximately 129 mg. each. Similarly prepared are tablets containing 2-amino-N-[(5-hydroxy-4H-pyran-4-on-2-yl)methyl]acetamide, and 2-amino-N[(5-hydroxy-4H-pyran-4-on-2-yl)methyl]propionamide, respectively.

| TABLET FORMULA | |
|---|---|
| INGREDIENT | MG. PER TABLET |
| 2-Aminomethyl-5-hydroxy-4H-pyran-4-one | 5 mg. |
| Calcium phosphate | 52 mg. |
| Lactose | 60 mg. |
| Starch | 10 mg. |
| Magnesium stearate | 1 mg. |
| 2-Amino-N-[(5-hydroxy-4H-pyran-4-on-2-yl)methyl]acetamide | 5 mg. |
| Calcium phosphate | 52 mg. |
| Lactose | 60 mg. |
| Starch | 10 mg. |
| Magnesium stearate | 1 mg. |

| TABLET FORMULA | |
|---|---|
| INGREDIENT | MG. PER TABLET |
| 2-Amino-N[(5-hydroxy-4H-pyran-4-on-2-yl)methyl]propionamide | 5 mg. |
| Calcium phosphate | 52 mg. |
| Lactose | 60 mg. |
| Starch | 10 mg. |
| Magnesium stearate | 1 mg. |

What is claimed is:

1. A compound having the structural formula:

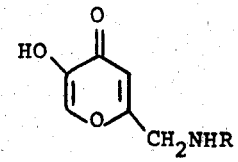

wherein R is hydrogen or an α-amino acid acyl moiety or a pharmaceutically acceptable salt thereof.

2. A compound according to claim 1 which is 2-aminomethyl-5-hydroxy-4H-pyran-4-one.

3. A compound according to claim 1 which is 2-amino-N-[(5-hydroxy-4H-pyran-4-on-2-yl)methyl]acetamide.

4. A compound according to claim 1 which is 2-amino-N-[(5-hydroxy-4H-pyran-4-on-2-yl)methyl]propionamide.

5. A pharmaceutical composition comprising a therapeutically effective amount in unitary dosage form of a compound having the formula:

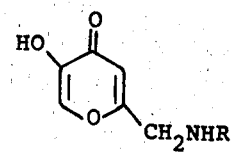

wherein R is hydrogen or an α-amino acid acyl moiety or a pharmaceutically acceptable salt thereof and a pharmaceutically acceptable carrier therefor.

6. A method of treatment of skeletal muscle hyperactivity comprising administering to a patient in need of such treatment a therapeutically effective amount of a compound having the formula:

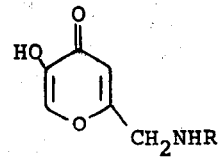

wherein R is hydrogen or an α-amino acid acyl moiety or a pharmaceutically acceptable salt thereof.

* * * * *